United States Patent
Schnaubelt et al.

(10) Patent No.: US 7,141,667 B2
(45) Date of Patent: Nov. 28, 2006

(54) 3-(4-PIPERIDINYL)-2,3,4,5-TETRAHYDRO-1,3-BENZODIAZEPIN-2(1H)-ONE

(75) Inventors: Juergen Schnaubelt, Biberach (DE); Werner Rall, Mittelbiberach (DE); Rainer Soyka, Biberach (DE); Norbert Birk, Rot a. d. Rot (DE); Ludwig Gutschera, Ulm (DE); Heidelore Heimroth, Bad Waldsee (DE); Thomas Krueger, Kisslegg (DE); Armin Proell, Maselheim (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 11/185,593

(22) Filed: Jul. 19, 2005

(65) Prior Publication Data

US 2006/0019946 A1   Jan. 26, 2006

(30) Foreign Application Priority Data

Jul. 23, 2004   (EP)   ................... 04017424

(51) Int. Cl.
*C07D 401/04*   (2006.01)
(52) U.S. Cl. ..................................... 540/500
(58) Field of Classification Search ................. 540/500
See application file for complete search history.

(56) References Cited

U.S. PATENT DOCUMENTS 3,474,090 A   10/1969   Wright, Jr.

FOREIGN PATENT DOCUMENTS

| CA | 2361939 | 9/2000 |
|---|---|---|
| WO | 0055154 | 9/2000 |

OTHER PUBLICATIONS

Mayer, P. et al; New Substituted 1-(2,3-Dihydrobenzo[1,4]dioxin-2-ylmethyl)piperidin-4-yl Derivatives with a2-Adrenoceptor Antagonist Activity; Journal of Medicinal Chemistry, 2000, vol. 43, pp. 3653-3664.

*Primary Examiner*—Bruck Kifle
(74) *Attorney, Agent, or Firm*—Michael P. Morris; Mary-Ellen M. Devlin; Alan R. Stempel

(57) ABSTRACT

The present invention relates to a process for preparing the compound 3-(4-piperidinyl)-2,3,4,5-tetrahydro-1,3-benzodiazepin-2(1H)-one of formula (I)

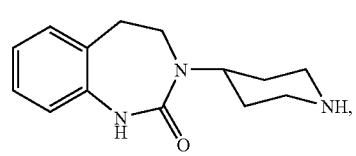

which is to be found as a structural element in CGRP-antagonists, which are particularly suitable for the oral treatment of migraine.

7 Claims, No Drawings

3-(4-PIPERIDINYL)-2,3,4,5-TETRAHYDRO-1,3-BENZODIAZEPIN-2(1H)-ONE

The present invention relates to a process for preparing the compound 3-(4-piperidinyl)-2,3,4,5-tetrahydro-1,3-benzodiazepin-2(1H-one of formula

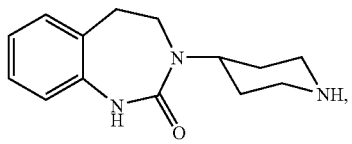

which can be found as a structural element in CGRP antagonists which are suitable primarily for the oral treatment of migraine.

Examples of compounds with CGRP-antagonistic properties which contain as structural element the compound of formula (I), are described in international patent applications PCT/EP97/04862, PCT/EP00/02004, PCT/EP00/13236, PCT/EP03/02417, PCT/EP03/11762 and PCT/EP03/11763.

2-Nitrophenylacetic acid may be used as a starting material for the compound of formula I. In a first step it is reacted with an equimolar solution of 4-amino-N-phenylmethylpiperidine in the presence of at least one equivalent, preferably 1.1 to 1.5 equivalents, particularly preferably 1.1 equivalents, of condensation agents such as carbonyldiimidazole, carbonyiditriazole, n-propanephosphonic anhydride, dicyclohexylcarbodiimide, thionyl chloride, TBTU O-(benzotriazol-1-yl)-N,N,N',N'-tetramethyluronium tetrafluoroborate or 1-ethyl-3-(3'-dimethylaminopropyl)-carbodiimide to form the 2-nitro-N-[1-(phenylmethyl)-4-piperidinyl]-phenylacetamide. Suitable solvents are polar aprotic solvents such as tetrahydrofuran, dimethoxyethane, toluene, dimethylformamide or N-methylpyrrolidinone. The product may be crystallised e.g. by diluting with water and worked up by filtration or centrifugation and drying.

In the following key step the 2-nitro-N-[1-(phenylmethyl)-4-piperidinyl]-phenylacetamide is first dissolved in a polar aprotic organic solvent, such as for example tetrahydrofuran or dimethoxyethane, and the carbonyl group is converted into a methylene group by the addition of at least one equivalent, preferably 2.0 to 4.0 equivalents, of a reducing agent. Suitable reducing agents are for example borane, lithium or sodium borohydride, optionally with the addition of at least 0.5 equivalents, preferably 2.0 to 4.0 equivalents, of a Lewis acid, an acid or a halogen, for example with the addition of sulphuric acid, chlorotrimethylsilane or iodine. The reduction may be carried out at temperatures of 20 to 70° C., preferably at 60 to 70° C.

Then the nitro group of the intermediate product N-[2-(2-nitrophenyl)ethyl]-1-(phenylmethyl)-4-amino-piperidine thus obtained is hydrogenated in the presence of a Raney nickel catalyst. For the hydrogenation the starting material is placed in dimethylformamide and the catalyst is added as an aqueous suspension. Advantageous conditions for the hydrogenation are temperatures of 20 to 60° C. and a excess hydrogen pressure of at most 3 bar. After the catalyst has been filtered off the hydrogenation product may be concentrated by distillation of the solvent. Then cyclisation is carried out by adding the crude product thus obtained to a suspension of at least one equivalent, preferably 1.1 to 1.75 equivalents, particularly preferably 1.1 equivalent, of a condensing agent, such as for example carbonyldiimidazole or carbonyiditriazole. Suitable solvents are polar aprotic solvents such as tetrahydrofuran, ethyl acetate, 2-methyltetrahydrofuran, dimethylformamide or N-methylpyrrolidinone. The 3-[1-(phenylmethyl)-4-piperidinyl]-2,3,4,5-tetrahydro-1,3-benzodiazepin-2(1H)-one thus obtained may be precipitated e.g. by diluting with water and alcohol, for example methanol, ethanol or isopropanol, preferably methanol, and worked up by filtration or centrifugation and drying.

If desired the intermediate product N-[2-(2-nitrophenyl)ethyl]-1-(phenylmethyl)-4-amino-piperidine may be precipitated and isolated in the form of a salt by the addition of at least 2 equivalents of an aqueous solution of a strong acid. Examples of suitable acids are hydrochloric acid, hydrobromic acid or sulphuric acid, particularly hydrochloric acid, whereby the dihydrochloride is obtained. For this purpose the reaction mixture is cooled to ambient temperature and combined with an alcohol, such as for example methanol, ethanol or isopropanol, preferably methanol. After the addition of an excess of the aqueous acid the mixture is refluxed again and then cooled once more. The reaction mixture is made alkaline with an aqueous solution of a base, for example lithium hydroxide, sodium hydroxide, ammonia or potassium hydroxide, and after phase separation the organic phase is combined with an excess of the aqueous acid, whereupon the desired salt crystallises out. The product may then be worked up by filtration or centrifugation and drying.

In a third step the benzyl protecting group of the 3-[1-(phenylmethyl)-4-piperidinyl]-2,3,4,5-tetrahydro-1,3-benzodiazepin-2(1H)-one is cleaved. To do this, the starting material is dissolved in a polar solvent, such as for example methanol, ethanol, water, acetone, tetrahydrofuran, dimethylformamide or propanol, and hydrogenated in a pressurised reactor. Pd/C or Pd(OH)$_2$ for example may be used as hydrogenating agents. Advantageous conditions for the hydrogenation are temperatures of 40 to 80° C. and an excess hydrogen pressure of at most 3 bar. After the catalyst has been filtered off the hydrogenation product 3-(4-piperidinyl)-2,3,4,5-tetrahydro-1,3-benzodiazepin-2(1H)-on of formula (I) may be crystallised by concentrating the solvent and subsequently adding acetone or water, then filtered off and dried.

Experimental Section

EXAMPLE 1

2-nitro-N-[1-(phenylmethyl)-4-piperidinyl]-phenylacetamide

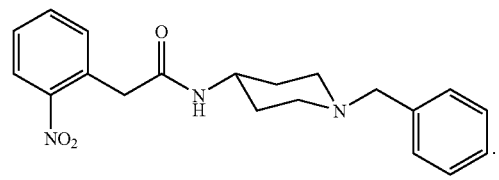

11.81 kg (72.87 mol, 1.1 eq) of 1,1-carbonyldiimidazole (CDI) are taken at 20° C. and 18 L tetrahydrofuran are added. Then 12.00 kg (66.24 mol, 1.0 eq) 2-nitrophenylacetic acid, dissolved in 24 L tetrahydrofuran, are added within 15 minutes. The feeder vessel is rinsed with 9 L tetrahydrofuran and the reaction mixture is stirred for 30 minutes (gas given off: $CO_2$). Then a vacuum of 300 mbar is applied twice in order to eliminate excess $CO_2$.

12.61 kg (66.24 mol, 1.0 eq) 4-amino-N-phenylmethylpiperidine in 6 L tetrahydrofuran are added to the solution at 20° C. (exothermic). After the reaction mixture has been added the resulting mixture is stirred for another 2 hours at 20° C. Then 144 L water are added, and after the addition of ¼ of the amount of water the solution is inoculated with 2-nitro-N-[1-(phenylmethyl)-4-piperidinyl]-phenylacetamide. The resulting suspension is cooled to 0 to 5° C. and stirred for a further hour in order to complete the crystallisation. Then the product is removed by centrifuging, washed with a cold mixture of 160 L water and 9 L tetrahydrofuran and dried at 45° C. in the drying cupboard with inertisation.

Yield: 18.21 kg (77.8% of theory)
Chemical purity according to HPLC: 99.8%

EXAMPLE 2

N-[2-(2-nitrophenyl)ethyl]-1-(phenylmethyl)-4-amino-piperidine-dihydrochloride

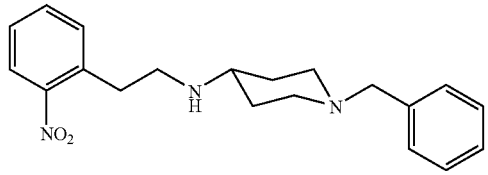

10.00 kg (28.29 mol, 1.0 eq) 2-nitro-N-[1-(phenylmethyl)-4-piperidinyl]-phenylacetamide from Example 1 are placed in 60 L tetrahydrofuran and heated to 60° C. 11.06 kg (101.84 mol, 3.6 eq) chlorotrimethylsilane and 14.79 kg (67.90 mol, 2.4 eq) of a 10% lithium borohydride solution in THF are metered in at 60 to 65° C. (gas given off) within 15 minutes. The reaction mixture is stirred for 4 hours, then cooled to 20° C. and combined with 7 L methanol. After the addition of 14.80 kg (121.65 mol, 4.3 eq) 30% industrial-grade hydrochloric acid the reaction mixture is refluxed for 2.5 hours, cooled to 20° C. and the pH is adjusted to 9.2 with 8.38 kg (104.67 mol, 3.7 eq) 50% industrial-grade sodium hydroxide solution. The aqueous phase is separated off, the organic phase is combined with 6.89 kg (56.58 mol, 2.0 eq) 30% industrial-grade hydrochloric acid (pH 1.5) and refluxed for 1 hour. The suspension obtained is cooled to 0° C. within 3 hours. To complete the crystallisation the mixture is stirred for 1 hour at 0° C. Then the product is removed by centrifuging, washed with 20 L tetrahydrofuran and dried at 50° C. in the drying cupboard with inertisation.

Yield: 7.78 kg (66.7% of theory)
Chemical purity according to HPLC: 99.3%

EXAMPLE 3

3-[1-(phenylmethyl)-4-piperidinyl]-2,3,4,5-tetrahydro-1,3-benzodiazepin-2(1 H)-one

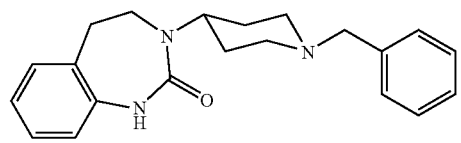

10.00 kg (24.25 mol, 1.0 eq) N-[2-(2-nitrophenyl)ethyl]-1-(phenylmethyl)-4-amino-piperidine-dihydrochloride from Example 2 are placed in 30 L each of toluene and water. 5.82 kg (72.75 mol, 3.0 eq) 50% industrial-grade sodium hydroxide solution are metered in and the two-phase mixture is stirred for 1 hour at 50° C. The aqueous phase is separated off, the organic phase is washed with 12 L water and then evaporated down in vacuo. The residue is combined with 50 L methanol. Some of the methanol used is distilled off. The remaining solution is hydrogenated at 50° C. in the presence of 860 g Raney nickel. The catalyst is filtered off and washed with 16 L methanol. The solvent is distilled off and the residue is combined with 30 L tetrahydrofuran. Half the tetrahydrofuran used is distilled off and the remaining solution is metered in at 20° C. to a suspension of 6.88 kg (42.44 mol, 1.75 eq) 1,1-carbonyldiimidazole in 15 L tetrahydrofuran within 1.5 hours. The mixture is stirred for 1 hour at this temperature. Then 20 L water are added, the mixture is inoculated and a further 17 L of water are added. The suspension obtained is cooled to 0° C. To complete the crystallisation the mixture is stirred for 1.5 hours at 0° C. Then the product is removed by centrifuging, washed with 30 L water and dried at 45° C. in the drying cupboard with inertisation.

Yield: 6.38 kg (78.4% of theory)
Chemical purity according to HPLC: 98.5%

EXAMPLE 4

3-[1-(phenylmethyl)-4-piperidinyl]-2,3,4,5-tetrahydro-1,3-benzodiazepin-2(1H)-one

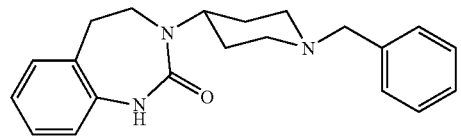

17.00 kg (48.10 mol, 1.0 eq) 2-nitro-N-[1-(phenylmethyl)-4-piperidinyl]-phenylacetamide from Example 1 are suspended in 170 L ethyleneglycol dimethyl ether and cooled to 0 to 5° C. At this temperature 7.28 kg (192.40 mol, 4.0 eq) sodium borohydride and then a solution of 9.91 kg (101.01 mol, 2.1 eq) industrial-grade sulphuric acid in 17 L ethyleneglycol dimethyl ether are added batchwise. After the addition has ended the mixture is rinsed with 6.8 L of ethyleneglycol dimethyl ether. Within 1 hour the reaction mixture is heated to 70° C. and stirred for 4 hours at this temperature.

After cooling to 55° C. a solution of 29 L water and 11.69 kg (96.20 mol, 2.0 eq) 30% industrial-grade hydrochloric acid is metered in. After the addition has ended the mixture is rinsed with 5 L water. Stirring is then continued for another 1.5 hours at 70° C. Then the reaction mixture is cooled to 20° C. and combined with 30.0 kg (375.18 mol, 7.8 eq) 50% industrial-grade sodium hydroxide solution and 17 L water. After the phase separation the organic phase is evaporated down in vacuo to leave an oil which is then combined with 43 L dimethylformamide.

The solution obtained as above is drained from the reactor into a container and transferred into the hydrogenating reactor. 1.35 kg of Raney nickel catalyst suspension, which have previously been combined three times with 3 L dimethylformamide and decanted off, are suspended in 3 L dimethylformamide and suction filtered. Then the mixture is hydrogenated at 3 bar at an internal temperature of 50° C., until no further uptake of hydrogen can be detected. The catalyst is filtered off and washed with 17 L dimethylformamide. Then at least 46 L of the solvent are distilled off in vacuo. If after this amount of distillation the water content of the distillate has not fallen below 1%, distillation is continued until the desired value is obtained.

8.58 kg (52.91 mol, 1.1 eq) 1,1-carbonyldiimidazole are taken and combined with 32 L dimethylformamide. Then at a temperature of 20° C. hydrating solution (from the preceding reaction step) is metered in within 2 hours. After 30 minutes stirring the mixture is checked to see whether the reaction is complete. Then it is heated to 50° C. and a mixture of 34 L methanol and 136 L water is metered in within 35 minutes. To complete the crystallisation another 34 L water are added at 50° C. and the suspension is cooled to 10° C. within 1 hour and stirred for 30 minutes at this temperature. Then the precipitate is removed by centrifuging, washed with 85 L water and dried at 50° C. in the drying cupboard.

Yield: 12.73 kg (78.9% of theory)
Chemical purity according to HPLC: 96.0%

EXAMPLE 5

3-(4-piperidinyl)-2,3,4,5-tetrahydro-1,3-benzodiazepin-2(1H)-one

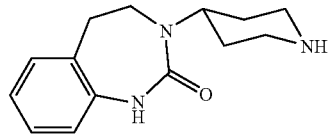

10.00 kg (29.81 mol, 1.0 eq) 3-[1-(phenylmethyl)-4-piperidinyl]-2,3,4,5-tetrahydro-1,3-benzodiazepin-2(1H)-one from Example 3 are dissolved in 100 L methanol, combined with 1.00 kg 10% Pd/C and hydrogenated in the pressurised reactor at 70° C. and 3 bar. After the uptake of hydrogen has ended the catalyst is filtered off and washed with 30 L methanol. The filtrate is concentrated in vacuo and the residue is suspended in 100 L acetone. Then it is refluxed, the suspension is stirred for 15 minutes at reflux temperature and half the acetone is distilled off under normal pressure. After distillation has ended the mixture is cooled to 0° C. and stirred for a further hour. The product is suction filtered, washed with 20 L acetone and dried at 50° C.

Yield: 6.17 kg (84.3% of theory)
Chemical purity according to HPLC: 99.8%

What is claimed is:
1. A process for preparing the compound of formula

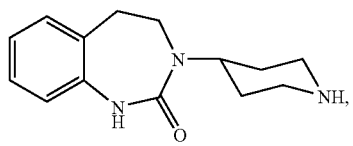

(I)

wherein,
(a) 2-nitrophenylacetic acid is reacted with 4-amino-N-phenylmethylpiperidine in the presence of condensing agents;
(b) the carbonyl group of the resulting 2-nitro-N-[1-(phenylmethyl) -4-piperidinyl]-phenylacetamide is converted into a methylene group by the addition of a reducing agent;
(c) after reduction of the nitro group in the presence of a Raney nickel catalyst, the intermediate product N-[2-(2-nitrophenyl)ethyl]-1-(phenylmethyl) -4-amino-piperidine obtained is cyclised by the addition of condensing agents to obtain 3-[1-(phenylmethyl)-4-piperidinyl]-2,3,4,5-tetrahydro -1,3-benzodiazepin-2(1H)-one and
(d) by cleaving the benzyl protecting group the 3-[1-(phenylmethyl) -4-piperidinyl]-2,3,4,5-tetrahydro-1,3-benzodiazepin-2(1H)-one is converted into the compound of formula (I).

2. The process according to claim 1, wherein in step (a) the 4-amino-N-phenylmethylpiperidine is added as a solution and the product obtained in the reaction is crystallised out by diluting with water.

3. The process according to claim 1, wherein in step (b) the 2-nitro-N-[1-(phenylmethyl)-4-piperidinyl]-phenylacetamide is dissolved in a polar aprotic organic solvent and the reduction is carried out at temperatures of 20 to 70° C., optionally with the addition of a Lewis acid, an acid or a halogen.

4. The process according to claim 1, wherein the starting compound in step (c) is placed in dimethylformamide, the catalyst is added as an aqueous suspension and hydrogenation is carried out at temperatures of from 20 to 60° C. and at an excess hydrogen pressure of at most 3 bar.

5. The process according to claim 1, wherein the starting material in step (d) is dissolved in a polar solvent and after the addition of a hydrogenating agent is hydrogenated in a pressurised reactor at temperatures of from 40 to 80° C. and at an excess hydrogen pressure of at most 3 bar.

6. The process according to claim 1, wherein the intermediate product N-[2-(2-nitrophenyl)ethyl]-1-(phenylmethyl)-4-amino-piperidine obtained in step (b) is precipitated in the form of a salt by the addition of an aqueous solution of a strong acid and isolated.

7. The process according to claim 4, wherein the product 3-[1-(phenylmethyl) -4-piperidinyl]-2,3,4,5-tetrahydro-1,3-benzodiazepin-2(1H)-one obtained is precipitated by diluting with water and alcohol.

* * * * *